United States Patent [19]

Cao

[11] Patent Number: 5,691,464

[45] Date of Patent: Nov. 25, 1997

[54] APPARATUS FOR HIGH OXYGEN CONCENTRATION MEASUREMENT USING LIMITING CURRENT OXYGEN SENSOR

[75] Inventor: Tuan Quoc Cao, Davenport, Iowa

[73] Assignee: Litton Systems, Inc., Davenport, Iowa

[21] Appl. No.: 796,084

[22] Filed: Feb. 5, 1997

[51] Int. Cl.[6] .................. G01N 27/00; G01N 1/22; G01M 15/00
[52] U.S. Cl. .................. 73/23.31; 73/23.21; 73/31.01; 422/83; 422/94; 204/406; 204/409
[58] Field of Search .................. 73/23.31, 116, 73/23.21, 23.32, 31.01; 422/83, 94; 204/153, 425, 409

[56] References Cited

U.S. PATENT DOCUMENTS

| | | | |
|---|---|---|---|
| 4,574,627 | 3/1986 | Sakurai et al. | 73/116 |
| 4,595,485 | 6/1986 | Takahashi et al. | 204/406 |
| 4,626,338 | 12/1986 | Kondo et al. | 204/406 |
| 4,839,019 | 6/1989 | Takahama et al. | 204/425 |
| 5,145,566 | 9/1992 | Logothetis et al. | 204/153.18 |
| 5,186,810 | 2/1993 | Nagai et al. | 204/425 |
| 5,270,009 | 12/1993 | Nakamori et al. | 422/83 |
| 5,297,432 | 3/1994 | Traina et al. | 73/864.34 |
| 5,524,472 | 6/1996 | Hotzel | 73/1 G |
| 5,569,838 | 10/1996 | Broedel et al. | 73/23.31 |
| 5,596,154 | 1/1997 | Baughman | 73/863.01 |

*Primary Examiner*—Hezron E. Williams
*Assistant Examiner*—J. David Wiggins
*Attorney, Agent, or Firm*—Michael H. Wallach

[57] ABSTRACT

A gas analysis apparatus using multiple orifices of preselected sizes to attain a calculated gas mixing ratio for diluting an oxygen sample to a concentration less than 95% prior to application to a limiting current oxygen sensor. The apparatus comprises a regulator for regulating the pressures of incoming flows of air and oxygen sample to be measured, a valve for allowing the concentration of the air sample to oxygen sample to be measured, and a system for calculating the air sample/oxygen sample mixing ratio based on the known air sample concentration and then, based on the known air concentration and calculated mixing ratio, calculating the unknown sample concentration from the output of the oxygen sensor.

8 Claims, 1 Drawing Sheet

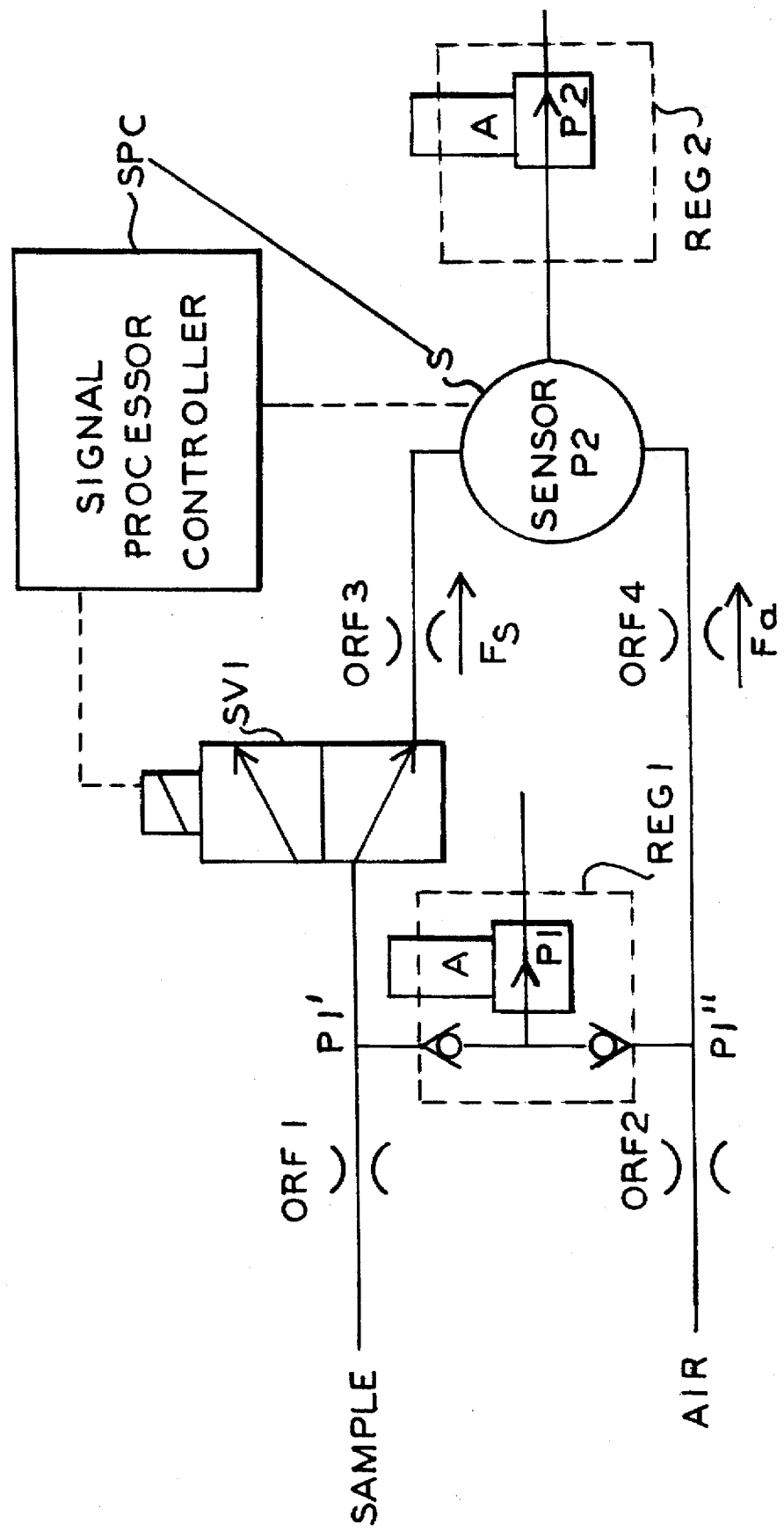

APPARATUS FOR HIGH OXYGEN CONCENTRATION MEASUREMENT USING LIMITING CURRENT OXYGEN SENSOR

FIELD OF THE INVENTION

The present invention relates in general to limiting current oxygen sensors, and more particularly to an apparatus for high oxygen concentration measurement using limiting current oxygen sensors.

BACKGROUND OF THE INVENTION

Solid state limiting current oxygen sensors are used in many applications, ranging from atmospheric measurements, combustion control, to oxygen concentrators for high performance aircraft. One such application is discussed in U.S. Pat. No. 5,071,453 assigned to Litton Systems, Inc. The basic structure comprises a zirconia electrolyte element comprising $ZrO_2$-$Y_2O_3$ in the shape of a disk which is heated to a temperature in the range of 400°–700° C. by means of an applied heating voltage of 1.7–3.0 VDC. A pair of porous platinum electrodes are provided on opposite sides of the zirconia disk to which a known voltage is applied, resulting in generation of a limiting current within the disk which is related to the oxygen concentration of the gas sample applied to the disk, as discussed below. The entire structure is encapsulated with diffusion holes on opposite sides of the disk.

Limiting current sensors are characterized by a number of advantages over other prior art sensors, such as longer operating lifetime (e.g. more than 10,000 hours), high accuracy (e.g. typically within ±0.5% $O_2$), and compact size.

It is well known that such sensors suffer from severe limitations when measuring very high oxygen concentrations. More particularly, the output characteristic for such sensors is given by the equation:

Output=C In (1-$O_2$%), where C is a constant.

Therefore, for $O_2$%=100%, the Output=C In (1-1)=∞. Accordingly, most sensors of this type are rated only for operation below 95% oxygen concentration. For a more detailed discussion of the limitations of prior art oxygen sensors of this type, see *Output Characteristics of Limiting Current Type Oxygen Sensor* by Akiyohsi Asada and Tohsio Usui in Proceedings of the 6th Sensor Symposium, 1986, pp. 237–260.

It is desirable in many applications to measure oxygen concentrations in excess of 95% by means of a limiting current oxygen sensor, in order to enjoy the advantages such sensors offer in terms of operating life, compact size, etc.

SUMMARY OF THE INVENTION

According to the present invention, an apparatus is provided for diluting an oxygen sample (which can be up to 100% O2), to a concentration less than 95% prior to application to a limiting current oxygen sensor. The apparatus comprises a regulator for regulating the pressures of incoming flows of air and oxygen sample to be measured, a valve for allowing the concentration of the air sample to be measured, and a system for calculating the air/sample mixing ratio based on the known air sample concentration and then, based on the known air concentration and calculated mixing ratio, calculating the unknown sample concentration from the output of the oxygen sensor.

In the preferred embodiment, a further regulator is provided to regulate the mixed pressure of air and oxygen sample applied to the oxygen sensor when operating with variable ambient pressure (e.g. at different altitudes in an aircraft).

BRIEF INTRODUCTION TO THE DRAWINGS

A detailed description of the preferred embodiment is provided herein below, with reference to the sole schematic illustration of an apparatus for high oxygen concentration measurement using a limiting current oxygen sensor.

DETAILED DESCRIPTION OF THE PREFERRED EMBODIMENT

Turning to FIG. 1, the apparatus according to the preferred embodiment is shown comprising a sample/air pressure regulator with check valve (REG1) which is connected to the sample and air sources via orifices ORF1 and ORF2. In normal operation the regulator REG1 is set to operate at a predetermined pressure P1, for regulating each of the sample and air pressures to approximately P1 (shown as P1' and P1", respectively).

A sliding solenoid valve (SV1) alternately connects the regulated oxygen sample flow to an orifice (ORF3) or connects the regulated air flow to the orifice ORF3 under control of a signal processor controller (SPC). The signal processor controller (SPC) is also connected to oxygen sensor (S) for performing calculations based on measured and known oxygen concentrations, as discussed in greater detail below. The regulated air flow also passes to a further orifice (ORF4). The orifices ORF3 and ORF4 are connected to the housing (chamber) of oxygen sensor (S).

Therefore, during normal operation, the regulated oxygen sample and air flows are applied to the sensor chamber where the mixing action takes place, whereas during air level check both sides of the sensor receive only the regulated air flow.

A second regulator (REG2) is preferably provided to regulate the mixed sample and air pressure P2 at the sensor S when the sensor is operated with variable ambient pressure (i.e. aircraft applications). At ground level the regulator REG2 is not required since P2=ambient pressure.

Since the sample pressure P1', air pressure P1", and P2 are constant, the flows across orifices ORF3 (flow indicated as Fs) and ORF4 (flow indicated as Fa) are constant. Hence, the mixing ratio of air and sample is also constant.

During calibration, a known gas (e.g. 99% $0_2$ calibration gas (Cc)) is applied to the sample port as sample along with air having known oxygen concentration (e.g. 20.9% $0_2$ air (Ca)). The oxygen concentration of air (Ca) is determined during calibration by energizing solenoid SV1, while the aircraft is on the ground. The mixture concentration is then recorded along with the known concentrations, for later use. Thus, if 99% $O_2$ is used as calibration gas (Cc), and the mixture reading is 68%, then Cc=99%, Cr=68% and Ca=20.9% oxygen in air are recorded as calibration parameters.

During in-flight sensing, an air level check is performed first (i.e. solenoid valve SV1 is energized), and the sensor S tests the air source concentration of oxygen (e.g. 20.7% $0_2$ air concentration (Ca')). This concentration is Used to calculate the sample concentration.

Next, the solenoid valve SV1 is de-energized such that the sensor S receives a mixture of air and sample (regulated flows Fa and Fs). By knowing the air concentration and mixing ratio, the unknown sample oxygen concentration can be calculated, from the output current of the oxygen sensor based on the diluted sample applied to the sensor S, according to the sensor output characteristic set forth above and using any one of a number of calculation methods. One of the simplest methods of calculation uses linear approximation. Using the example concentrations discussed above, the linear approximation method is as follows:

1-During calibration with a diluted mixture of 99% oxygen calibration gas (Cc) and 20.9% oxygen air (Ca); the calibration reading (Cr) is 68%. All of these concentrations are stored as calibration parameters for later retrieval, as discussed above.

2-During normal operation (e.g. in-flight testing), assuming that the mixture concentration reading (Cm) is 68.3%, and assuming that during the air check, the air concentration (Ca') was 20.7% oxygen, then 3-Using linear approximation, the sample concentration (Cs) is:

$$Cs = (Cm - Ca')*(Cc - Ca)/(Cr - Ca) + Ca'$$

or $$Cs = (68.3 - 20.7)*(99 - 20.9)/(68 - 20.9) + 20.7$$
$$= 99.6\%$$

As discussed above, the sensor S is capable of measuring oxygen concentrations from 0 to 95%. Depending on the sizes of the orifices selected, the diluted or mixed sample will have an oxygen concentration between 25 and 95%, and preferably between 50 and 80%. The mixing ratio depends on the sample and air flows (Fs and Fa). The flows depend on orifice sizes and the differential pressures between P1' and P2 and between P1" and P2. It is well within the skill of a person of ordinary skill in the art to calculate the sizes of the orifices based on desired flows or mixing ratio.

Alternatives and modifications of the invention are possible without departing from the sphere and scope of the invention as set forth in the claims appended hereto.

I claim:

1. An gas analysis apparatus for measuring high concentrations of oxygen, comprising:

a sample port for receiving a sample flow of one of either a calibration gas having a known oxygen concentration (Cc) or a sample gas having an unknown oxygen concentration (Cs) of up to 100%;

an ambient air port for receiving an air flow of ambient air having predetermined oxygen concentration (Ca);

a limiting current oxygen sensor having inputs connected to said sample port and said ambient air port for receiving a diluted oxygen mixture of said sample flow and said air flow in a known proportion and in the event said sample flow is calibration gas generating a calibration reading (Cr) indicating oxygen content in said mixture of calibration gas and air flow, and in the event said sample flow is sample gas generating a mixture concentration reading (Cm) indicating oxygen content in said mixture of sample gas and air flow; and a controller connected to said limiting current oxygen sensor for receiving and storing said known oxygen concentration (Cc) of said calibration gas, said predetermined oxygen concentration (Ca) of said air flow, said calibration reading (Cr) and said mixture concentration reading (Cm) and in response calculating said unknown oxygen concentration (Cs) in said sample gas.

2. The apparatus of claim 1, further comprising a regulator connected to said sample port and said ambient air port for regulating each said sample flow and said air flow to a predetermined pressure.

3. The apparatus of claim 2, further comprising an additional regulator for further regulating the pressure of said mixture to a second predetermined pressure when the sensor is operated with variable ambient pressure.

4. The apparatus of claim 2, further comprising a valve connected to a first input of said sensor and to said regulator for selecting one of either (i) said sample flow or (ii) said air flow to said sensor, a second input of said sensor being connected to said ambient air port, whereby said sensor measures oxygen concentration (Cm) of said mixture when said valve selects said sample flow and said sensor measures oxygen concentration (Ca) of said air flow when said valve selects said air flow.

5. The apparatus of claim 1, wherein said controller further comprises means for calculating said unknown oxygen concentration (Cs) in said sample gas via a mathematical operation utilizing linear approximation.

6. The apparatus of claim 5, wherein said means for calculating implements said linear approximation as follows:

$$Cs = \frac{(Cm - Ca)*(Cc - Ca)}{Cr - Ca} + Ca.$$

7. A gas analyser method for measuring high oxygen concentrations of up to 100% in a sample gas, using a limiting current oxygen sensor, comprising the steps of:

applying a with mixture known proportions of calibration gas having a known oxygen concentration (Cc) and ambient air having a known oxygen concentration (Ca) to said limiting current oxygen sensor which, in response generates a calibration reading (Cr) indicating oxygen content in said mixture of calibration gas and air;

storing said known oxygen concentrations (Cc and Ca) and said calibration reading (Cr);

applying a diluted oxygen mixture of said sample gas and ambient air in a known proportion to said limiting current oxygen sensor which, in response generates a mixture concentration reading (Cm) indicating oxygen content in said mixture of sample gas and air;

storing said mixture concentration reading (Cm);

retrieving said known oxygen concentrations (Cc and Ca), said calibration reading (Cr) and said mixture concentration reading (Cm); and calculating oxygen concentration (Cs) in said sample gas as follows:

$$Cs = \frac{(Cm - Ca)*(Cc - Ca)}{Cr - Ca} + Ca.$$

8. The method of claim 7, further comprising the steps of separately applying said ambient air to said limiting current sensor which, in response generates an adjusted air concentration reading (Ca') indicating oxygen content in said ambient air and calculating oxygen concentration (Cs) in said sample gas as follows:

$$Cs = \frac{(Cm - Ca)*(Cc - Ca)}{Cr - Ca} + Ca'.$$

* * * * *

UNITED STATES PATENT AND TRADEMARK OFFICE
CERTIFICATE OF CORRECTION

PATENT NO. : 5,691,464
DATED : November 25, 1997
INVENTOR(S) : Tuan Quoc Cao

It is certified that error appears in the above-indentified patent and that said Letters Patent is hereby corrected as shown below:

Column line 39, should read as follows:

--1. A gas analysis--

Column line 28, should read as follows:

--7. A gas analysis method--

Column line 31, should read as follows:

--applying a mixture with known proportions--

Signed and Sealed this

Fifteenth Day of June, 1999

Attest:

Q. TODD DICKINSON

*Attesting Officer*   Acting Commissioner of Patents and Trademarks